United States Patent
Alper et al.

[19]

[11] Patent Number: 6,024,822
[45] Date of Patent: Feb. 15, 2000

[54] METHOD OF MAKING DISPOSABLE NONWOVEN ARTICLES WITH MICROWAVE ACTIVATABLE HOT MELT ADHESIVE

[75] Inventors: Mark D. Alper, Mukwonago; Diane M. Strelow, Waukesha, both of Wis.

[73] Assignee: Ato Findley, Inc., Wauwatosa, Wis.

[21] Appl. No.: 09/020,722

[22] Filed: Feb. 9, 1998

[51] Int. Cl.$^7$ .................................................. B32B 31/28
[52] U.S. Cl. .................................. 156/273.3; 156/275.7; 156/283; 156/320; 604/365; 604/379
[58] Field of Search .................... 156/62.2, 62.6, 156/163, 164, 273.3, 273.7, 275.7, 283, 320, 324, 324.4, 272.2; 219/759; 604/365, 366, 379, 385.2, 358

[56] References Cited

U.S. PATENT DOCUMENTS

| | | | |
|---|---|---|---|
| 2,476,282 | 7/1949 | Castellan ................................. | 156/283 |
| 2,992,149 | 7/1961 | Drelich .................................... | 156/283 |
| 4,219,024 | 8/1980 | Patience et al. ........................ | 604/366 |
| 4,339,295 | 7/1982 | Boretos et al. ....................... | 156/275.7 |
| 4,818,315 | 4/1989 | Hellgren et al. ........................ | 156/62.2 |
| 4,906,497 | 3/1990 | Hellmann et al. ......................... | 428/49 |
| 5,089,556 | 2/1992 | Tabor et al. .............................. | 525/64 |
| 5,238,975 | 8/1993 | Johnson et al. .......................... | 523/137 |
| 5,334,446 | 8/1994 | Quantrille et al. ...................... | 428/284 |
| 5,681,305 | 10/1997 | Korpman ................................. | 604/390 |
| 5,750,607 | 5/1998 | Gerard et al. ............................ | 524/271 |
| 5,877,097 | 3/1999 | West et al. ............................... | 442/327 |

FOREIGN PATENT DOCUMENTS

WO 97/48779  12/1997  WIPO .
WO 99/22686   5/1999  WIPO .

*Primary Examiner*—Michael W. Ball
*Assistant Examiner*—Michael A Tolin
*Attorney, Agent, or Firm*—Andrus, Sceales, Starke & Sawall

[57] ABSTRACT

A method of utilizing microwave energy in the manufacture of disposable nonwoven absorbent articles such as diapers and feminine care products. More specifically, the traditional hot melt adhesives utilized in the production of disposable nonwoven absorbent articles are replaced by adhesives that are microwave sensitive, and which can be activated by microwave energy to provide strong bonds for the finished article.

31 Claims, 3 Drawing Sheets

METHOD OF MAKING DISPOSABLE NONWOVEN ARTICLES WITH MICROWAVE ACTIVATABLE HOT MELT ADHESIVE

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates to hot melt adhesives, and more particularly, to a method of utilizing microwave activatable hot melt adhesives in the manufacture of disposable nonwoven articles.

Nonwoven fabric is comprised of an interlocking fiber network, and is employed in the construction of disposable goods. Specific applications of nonwovens have included disposable diapers, sanitary napkins, pantyshields, surgical drapes, hospital pads, adult incontinence products and the like.

In such applications it is generally necessary to adhere a substrate composed of nonwoven material, tissue, absorbent fluff, superabsorbent materials, elastic materials or the like to another substrate. This second substrate may be another nonwoven fabric, tissue, fluff, superabsorbent core, or polyolefin materials such as a polyethylene or polypropylene layer. Typically, a hot melt adhesive has been used to bond such substrates together since there is no evaporation step necessary during manufacture, as would be the case for water-based or solvent-based adhesives. Suitable hot melt adhesives must posses the appropriate bond strength to adhere the substrates involved, and must also possess good flexibility, no staining or bleedthrough, suitable viscosity and open time to function on commercial equipment, acceptable stability under storage conditions, and acceptable thermal stability under normal application conditions.

Many different polymers have been used in hot melt adhesives employed in the construction of disposable nonwoven goods. In this regard, typical hot melt adhesives have employed polymers which have included S-I-S (styrene-isoprene-styrene); SBS (styrene-butadiene-styrene); SEBS (styrene-ethylene-butylene-styrene); EVA (ethylene-vinyl-acetate); and APAO (amorphous-poly-alpha-olefin). While these polymers, when properly blended, provide acceptable adhesion between most substrates employed in typical nonwoven construction such as diapers, they have had several shortcomings which have detracted from their usefulness.

One of the most noteworthy shortcomings of prior hot melt adhesives concerns open time, i.e. the time between application of the hot melt adhesive onto a substrate and before contact with the second substrate to which the first substrate is to be bonded. This time period results in cooling of the adhesive, and thus less flow of the adhesive occurs when in contact with the other substrate. This results in a weaker bond than desired in many circumstances. Thus, it is important in nonwoven constructions to insure that the hot melt adhesive is as hot as possible when in contact with the two substrates to be bonded so that sufficient flow of the adhesive into the substrates occurs resulting in the strongest possible bonds.

Another shortcoming of prior art hot melt adhesives concerns thermal stability under normal application conditions. Since hot melt adhesives must be melted prior to application, many hot melt adhesives cannot be used for bonding substrates which are typically employed in the construction of nonwoven articles due to their lack of heat stability. Thus, although many hot melt adhesives are known that would provide strong bonds with substrates such as polyethylene, polypropylene, nonwoven materials, tissue, fluff or the like, they are not typically employed in the construction of nonwoven articles due to unacceptable thermal stability. Thus, it would be desirable to utilize a method in the construction of nonwoven articles which would allow for the use of hot melt adhesives without regard to their heat stability.

Microwave activatable hot melt adhesives are known in the art. Attempts to render hot melt adhesives more sensitive to microwave radiation involve the addition of inorganic materials such as carbon fibers, carbon black or graphite to aid base hot melt adhesive such as that proposed in U.S. Pat. No. 4,906,497. Another method is disclosed in U.S. Pat. No. 5,238,975 which incorporates metals such as tungsten, chromium, aluminum, copper, titanium, titanium nitride, molybdenum disilicide, iron and nickel. Either of these approaches, however, has serious limitations. Some of these problems include the fact that the added materials settle out in the melt due to their weight, and may cause pump abrasion as well as filter or nozzle clogging. Some also represent potential fire and explosion hazards.

BRIEF SUMMARY OF THE INVENTION

A method of utilizing microwave energy in the manufacture of disposable nonwoven absorbent articles such as diapers and feminine care products. More specifically, the traditional hot melt adhesives utilized in the production of disposable nonwoven absorbent articles are replaced by adhesives that are microwave sensitive, and which can be activated by microwave energy to provide strong bonds for the finished article.

In one aspect of the invention, there is provided a method of bonding absorbent material such as fibers together for use as an absorbent core of a disposable nonwoven absorbent article. This may be accomplished by providing a suitable absorbent material such as cellulosic material, superabsorbent polymer or combinations thereof, mixing a microwave activatable adhesive with said absorbent material, forming the absorbent material and adhesive into a non-self-supporting absorbent core, and subjecting the core and adhesive to microwaves to activate the adhesive and bond the absorbent material together to form a cohesive, self-supporting absorbent core. More specifically, a powdered microwave sensitive adhesive could be mixed into the absorbent core material prior to being formed into a core so that the powdered adhesive is dispersed throughout the absorbent material forming the core. Once formed, microwaves directed at the core will be preferentially absorbed by the adhesive which will allow bonding of the absorbent material throughout the core, rather than just at the surface as is commonly performed in the prior art, to allow for better core integrity and a cohesive self-supporting finished core.

In another embodiment, the microwave sensitive adhesive may be utilized to bond the core to another substrate utilized in the disposable nonwoven absorbent article. This other substrate could be another layer of nonwoven fabric, tissue, absorbent fluff, a fluid impervious backsheet composed of a polyolefin such as polyethylene or polypropylene, or combinations thereof. This may be accomplished by first forming an absorbent core, applying a substrate to at least one surface of the absorbent core, and thereafter subjecting the core and adhesive to microwaves to activate the adhesive and bond the substrate to the core. The adhesive may be mixed with the fluff when forming the absorbent core, or applied to one or both of the mating surfaces of the core and substrate, or may be preapplied or coated onto the substrate prior to use and later activated during production of the finished article.

In yet another embodiment of the present invention, the method includes bonding a first substrate to a second substrate in the manufacture of disposable nonwoven absorbent articles. In this embodiment, first and second substrates to be bonded together are fed toward a laminating station, a microwave activatable adhesive is applied to a surface of at least one of the substrates prior to reaching the laminating station, so that when combined and subjected to microwave energy, the two substrates are bonded together. The adhesive may be subjected to the microwaves prior to forming the laminate, subsequent to forming the laminate, or simultaneously with foring the laminate.

Advantageously, the present method eliminates the disadvantage of "open time," i.e. the period between application of adhesive to the primary substrate and combination of that substrate with a second substrate. During that period of time, the adhesive cools and the bond formed is not as strong as it could have been if no cooling occurred. In the present method, the microwave sensitive adhesive can be applied to the substrate and then activated at a specifically desired time so that stronger bonds result since the adhesive is hotter when in contact with the substrates resulting in high flow into the substrates. A secondary benefit of decreased energy consumption may also result since microwave heating is more efficient than conventional electric resistance heating of the adhesives. In addition, a broader range of adhesives may be utilized in the construction of disposable nonwoven absorbent articles since the present method enables the use of adhesives without regard to their heat stability since no preliminary melt period is required.

DETAILED DESCRIPTION OF THE INVENTION

As used herein, the term "diaper" refers to an absorbent article typically worn by infants, young children and incontinent adult persons. As readily understood such an absorbent article is worn about the lower torso of the wearer and is held in place about the wearer's hips. It should be understood, however, that the present invention is also applicable to other absorbent articles such as training pants, incontinent products such as briefs and undergarments, feminine care products such as sanitary napkins and pantyliners, medical products, such as surgical drapes, and the like.

As used herein, the term "absorbent article" refers to a device or product which absorbs and contains body fluids and exudates such as urine. More specifically, this term refers to such devices or articles that are worn against or in proximity to the body of a wearer to absorb and contain various fluids and exudates discharged from the body. The term "disposable" is used herein to describe absorbent articles which are to be discarded after a single use. Such articles are not intended to be laundered or otherwise re-used as an absorbent article. Preferred embodiments of absorbent articles of the present invention are diaper 10 schematically shown in FIG. 1 and feminine care pad 11 schematically illustrated in FIG. 3.

Figure 1:
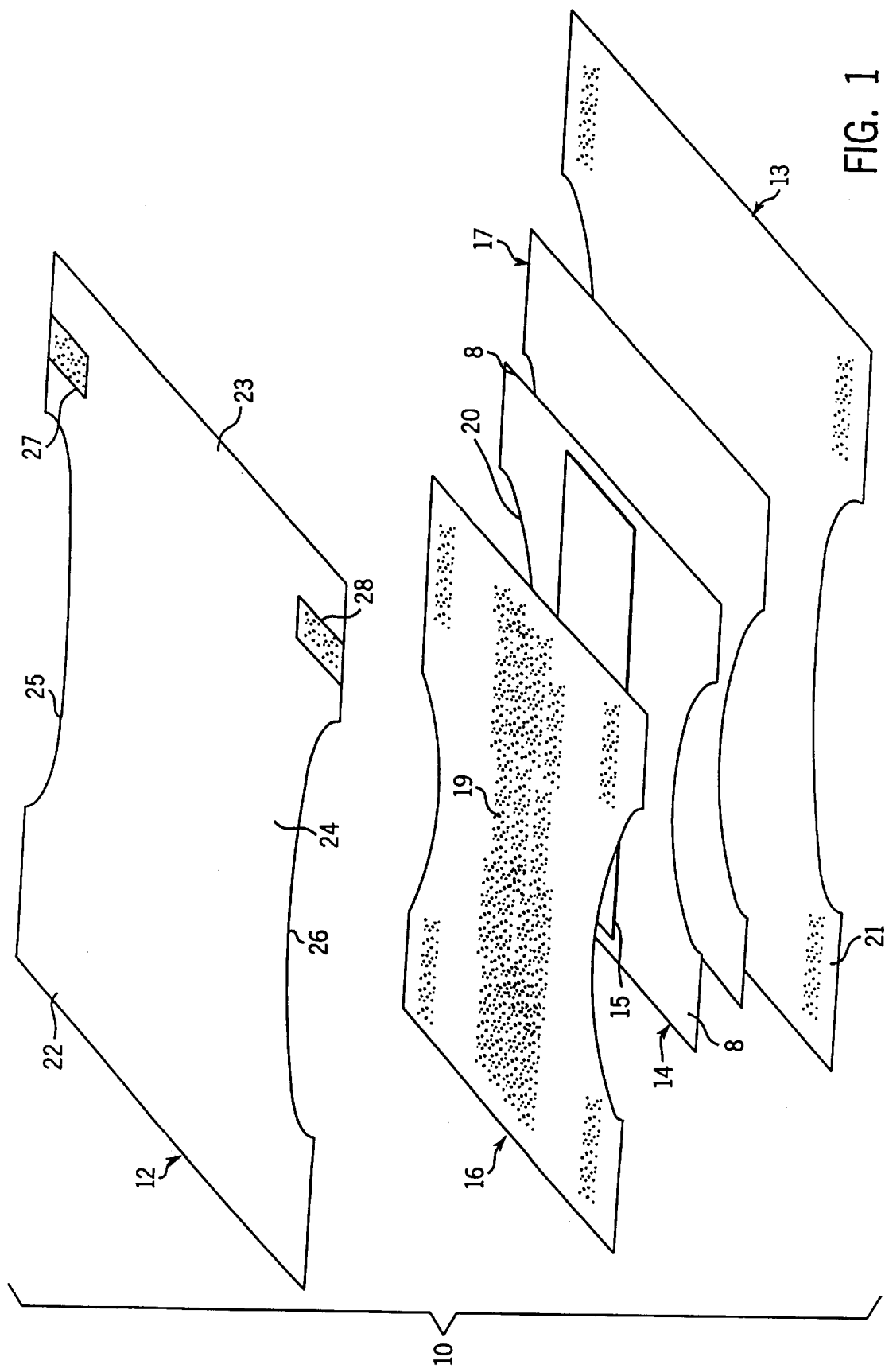
FIG. 1 is a schematic exploded, perspective view of a disposable diaper incorporating a microwave activatable hot melt adhesive constructed in accordance with the method of the present invention.
Figure 2:
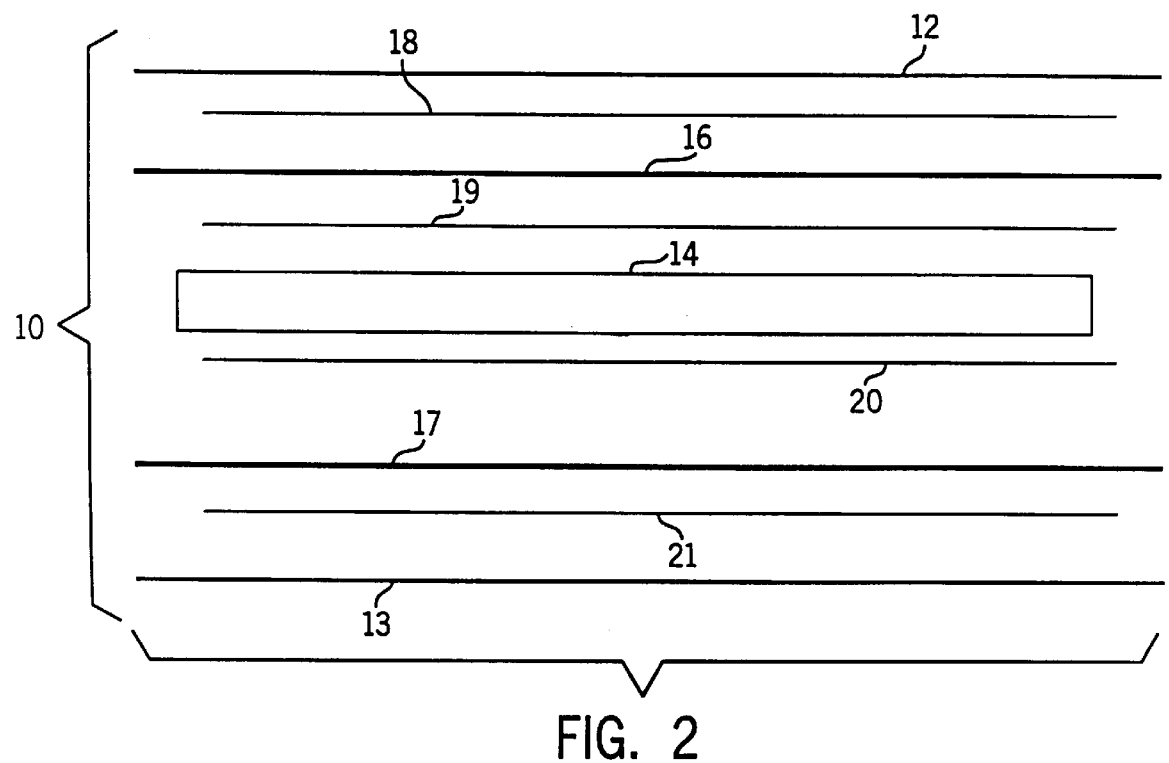
FIG. 2 is a schematic cross sectional view of the diaper of FIG. 1.

Referring now to FIGS. 1 and 2 there is illustrated in FIG. 1 an exploded view of various substrates comprising diaper 10 in its flat, uncontracted state with portions of the structure being shown schematically to more clearly show the construction of diaper 10. FIG. 2 schematically illustrates in cross section the multiple layers or substrates of diaper 10.

As shown, diaper 10 comprises multiple layers of sheet material or substrates adhesively bonded together to form the absorbent article. More specifically, diaper 10 includes a fluid pervious nonwoven topsheet 12 and a fluid impervious backsheet 13 (typically composed of a polyolefin material such as polyethylene or polypropylene) joined with topsheet 12. An absorbent core 14 is positioned between topsheet 12 and backsheet 13. Absorbent core 14 may be comprised of fluff 8 and, optionally, a centrally disposed superabsorbent polymer (SAP) material 15. Fluff 8 is typically composed of absorbent fibers such as cellulose fibers, but may also include other absorbent natural or synthetic fibers and/or materials. Diaper 10 may also include a top tissue layer 16 disposed between topsheet 12 and core 14 as well as a bottom tissue layer 17 disposed between backsheet 13 and core 14. As shown best in FIG. 2, each substrate can be bonded to an adjacent substrate by a layer of adhesive formulated to be microwave activatable in accordance with the present invention. For example, nonwoven topsheet 12 is bonded to top tissue layer 16 by a layer of adhesive 18 applied to the underside of topsheet 12. In turn, top tissue layer 16 is bonded to core 14 by a layer of adhesive 19. Core 14 is bonded to bottom tissue layer 17 by a layer of adhesive 20 and bottom tissue layer 17 in turn is bonded to a backsheet 13 by a layer of adhesive 21 applied to the upper surface of backsheet 13. In addition, the absorbent fibers of core 14 themselves may be bonded together to form a cohesive, self-supporting absorbent core, as will hereinafter be explained. The adhesive may be sprayed, spiral sprayed, melt blown, slot applied or may be applied as a bead depending upon the location and the type of bond desired. Also, the adhesive is dry in its neat form when mixed with fluff 8 or applied to a substrate. In its neat form, i.e. "dry", the adhesive may take the form of powder, flakes, grains, fibers or the like.

As noted above, the absorbent core 14 may contain discrete particles of a superabsorbent material. Superabsorbents are those materials which, upon contact with liquids such as water and body fluids, imbibe and retain such liquids and thereby form hydrogels. In this manner, liquids discharged into the absorbent core 14 can be acquired and held by the particles, thereby providing enhanced absorbent capacity and/or improved liquid retention performance.

The particles of superabsorbent material can be of any desired shape, e.g. spiral or semi-spiral, cubic, rod-like, polyhedral, spherical, etc. Shapes having a large greatest dimension/smallest dimension ratio, such as needles, flakes, and fibers, may also be used herein. Particles also include conglomerates of individual particles. Preferred superabsorbent materials for use in the present invention are "nonfibrous" particles such that the length to diameter ratio of the particulate material is about 10 or less, typically about 1 or less.

The superabsorbent can be an inorganic material such as a silica gel or an organic compound such as a cross-linked polymer. However, superabsorbent will generally comprise a substantially water-insoluble, slightly cross-linked, partially neutralized, hydrogel-forming polymer material. Such absorbent gelling materials can be prepared from polymerizable, unsaturated, acid-containing monomers.

Suitable unsaturated acidic monomers for use in preparing the absorbent gelling materials used include those described in U.S. Pat. No. RE 32,649. Preferred monomers include acrylic acid, methacrylic acid, and 2-acrylamido-2-methyl propane sulfonic acid, with acrylic acid being more preferred. The polymeric component formed from the unsaturated, acid-containing monomers may be grafted onto other types of polymer moieties such as starch or cellulose. Preferred absorbent gelling materials which can be prepared from conventional types of monomers include hydrolyzed acrylonitrile grafted starch, acrylic acid grafted starch, polyacrylates, maleic anhydride copolymers and combinations thereof, with polyacrylates and acrylic acid grafted starch being most preferred.

As shown best in FIG. 1, diaper 10 includes a pair of opposite waist panels 22, 23 interconnecting a crotch portion 24. Crotch portion 24 in turn includes a pair of opposite elasticized leg cuffs 25, 26. The waist panels 22, 23 are held together when diaper 10 is worn by a user by a fastening system which is illustrated in FIG. 1 as a pair of releasable tape tabs 27, 28.

Figure 3:
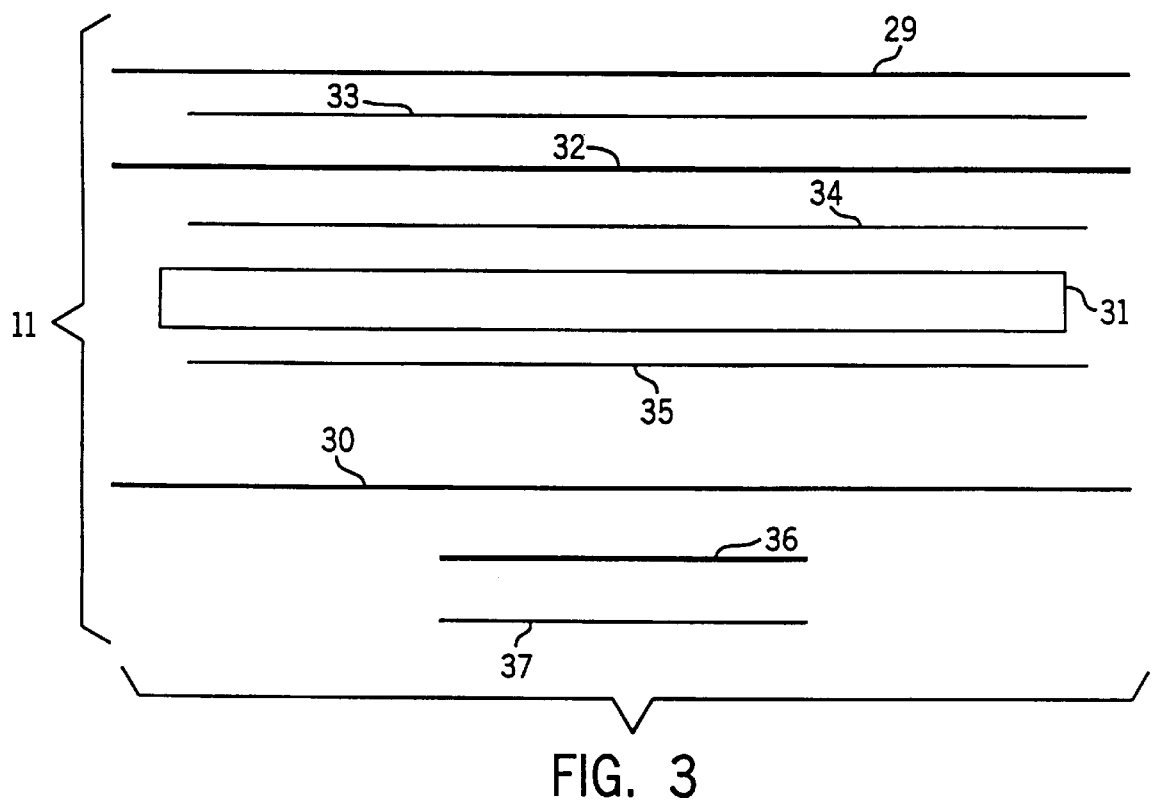
FIG. 3 is a schematic cross sectional view of a disposable feminine care pad incorporating a hot melt adhesive constructed in accordance with the method of the present invention.

Referring now to FIG. 3, there is illustrated an absorbent article illustrating a typical feminine care pad 11. Pad 11 comprises multiple layers of sheet material or substrates bonded together to form the absorbent article. More particularly, pad 11 includes a fluid pervious nonwoven topsheet 29 and a fluid impervious backsheet 30 (typically composed of a polyolefin material such as polyethylene or polypropylene) joined with topsheet 29. An absorbent core is positioned between topsheet 29 and backsheet 30. Absorbent core 31 may be comprised of fluff and/or super absorbent (SAP) material. Fluff 8 is typically composed of absorbent fibers such as cellulose fibers, but may also include other absorbent natural or synthetic fibers and/or materials. Pad 11 may also include a top tissue layer 32 disposed between topsheet 29 and core 31. As shown in FIG. 3, each substrate is bonded to an adjacent substrate by a layer of adhesive formulated to be microwave activatable in accordance with the present invention. For example, nonwoven topsheet 29 is bonded to top tissue layer 32 by a layer of adhesive 33 applied to the underside of topsheet 29. In turn, top tissue layer 32 is bonded to core 31 by a layer of adhesive 34. Finally, core 31 is bonded to backsheet 30 by a layer of adhesive 35 applied to the upper surface of backsheet 30. In addition, the absorbent fibers of core 14 themselves may be bonded together to form a cohesive, self-supporting absorbent core, as will hereinafter be explained. The adhesive may be sprayed, spiral sprayed, melt blown, slot applied or may be applied as a bead depending upon the location and the type of bond desired. Also, the adhesive may be dry when mixed with fluff 8 or applied to a substrate. When dry, the adhesive may take the form of powder, flakes, grains, fibers or the like. In the embodiment illustrated in FIG. 3, there is also a layer of adhesive 36 applied to the bottom side of backsheet 30 and release paper 37 covering adhesive 36. Thus, when paper 37 is removed to expose adhesive 36, adhesive layer 36 may be utilized to attach pad 11 to an undergarment worn by the user, as is conventional and well known in the art.

Figure 4:
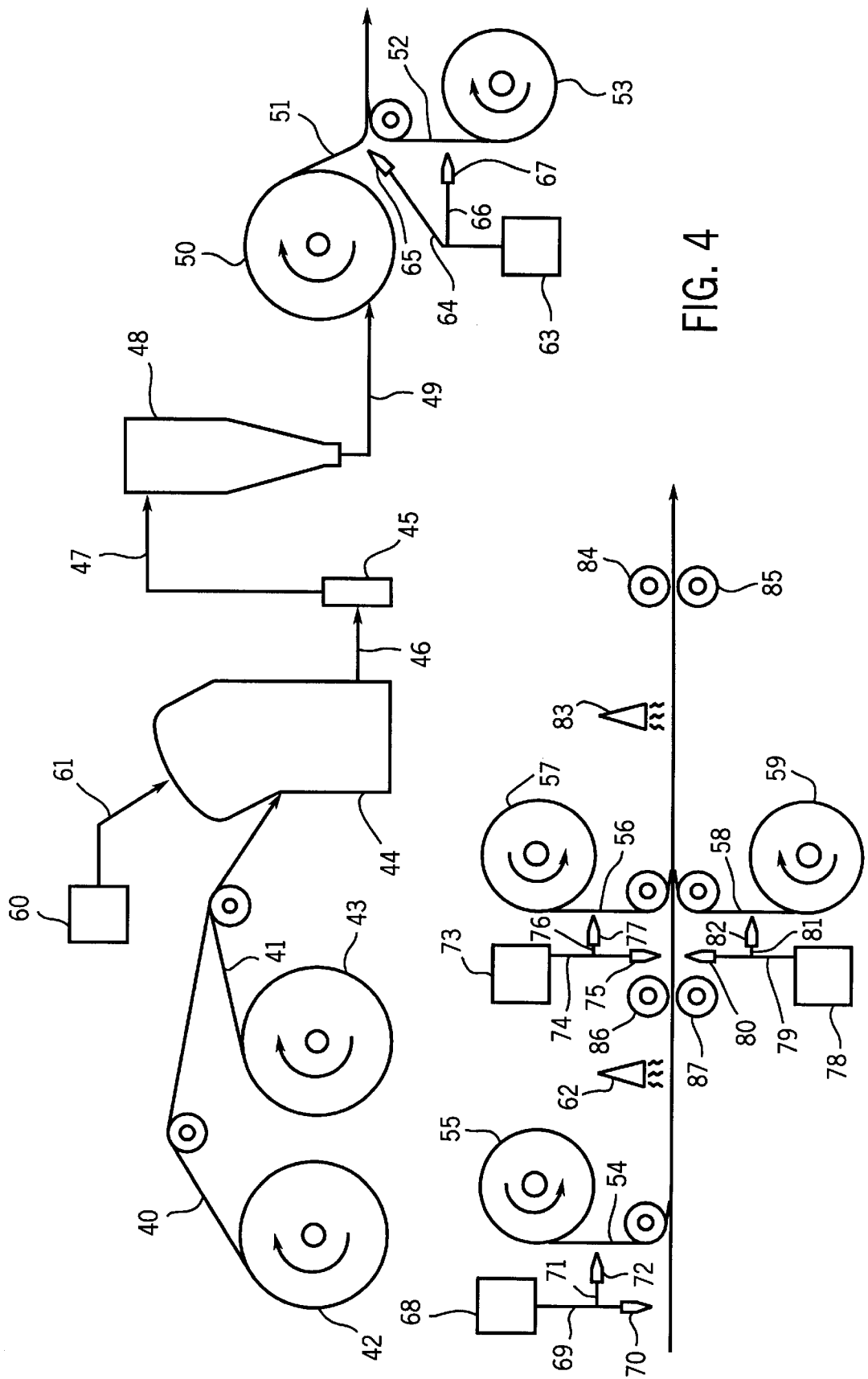
FIG. 4 is a schematic illustration of a system for manufacturing disposable feminine care pads embodying the method.

Referring now to FIG. 4, there is schematically illustrated a system for manufacturing disposable feminine care pads which embodies the method of the present invention. More specifically, sheets 40 and 41 of absorbent material, typically compacted cellulose fibers, are fed from storage rolls 42 and 43 respectively into a hammermill 44 which shreds the sheets 40 and 41 to form fluff. The fluff is then air conveyed via blower 45 through lines 46 and 47 into a cyclone 48 which homogeneously mixes the fluff with air. The fluff and air mixture is then fed via line 49 to a roll 50 which forms the fluff into an absorbent core. As is conventional, roll 50 includes a screen which has the preformed shape of the core formed therein, and the interior of roll 50 is subjected to a vacuum which draws the fluff from line 49 onto the screen to form the core. As roll 50 rotates, a portion of the interior eventually becomes subject to positive pressure which results in the core being "blown off" the surface of the screen. At this time, the core is substantially non-self-supporting and thus, needs to be supported by a substrate. When making feminine care products such as sanitary napkins, core 51 is supported by a tissue substrate 52 which is fed from storage roll 53. The core 51 supported by tissue layer 52 is then fed downstream where a second tissue layer 54 being fed from drum 55 is applied to the upper, surface of core 51. Finally, a nonwoven topsheet 56 fed from roll 57 is applied over tissue layer 54, and an impervious backsheet 58 fed from roll 59 is applied over tissue layer 52 to form the laminated structure illustrated in FIG. 3. The laminated structure is then fed downstream to be further processed into a sanitary napkin. Likewise, if the schematic illustration of the system illustrated in FIG. 4 is utilized to produce diapers, the laminate structure is also fed downstream to be further processed into the diaper illustrated in FIGS. 1 and 2.

The system illustrated in FIG. 4 and described up to this point is conventional and in standard use in the manufacture of feminine care pads and diapers. What is not standard or conventional, however, is the use of microwave sensitive adhesives in the process described and illustrated in FIG. 4 to bond various components and substrates together. More specifically, in one embodiment, a microwave activatable adhesive may be fed from a source 60 via line 61 into hammermill 44. This adhesive would be dry when mixed with the fluff being formed in hammermill 44. The dry adhesive may be in the form of powder, flakes, grains, fibers or the like. The dry adhesive would then be homogeneously mixed with the fluff being shredded in hammermill 44 as the fluff and adhesive is air conveyed through blower 45 and cyclone 48. Thus, when core 51 is formed on drum 50, the microwave sensitive adhesive is intimately and homogeneously mixed therewith. Thereafter, a microwave generator 62 is located downstream from drum 50 so that as core 51 passes through the microwaves generated, the adhesive absorbs the energy and is activated or melted to allow bonding of the core fibers throughout the core to provide a cohesive self-supporting core.

In addition to providing a method of bonding absorbent fibers together for use as an absorbent core, the present method also provides a method of bonding the absorbent core to another substrate. In this embodiment, microwave activatable adhesive may be sprayed from a source 63 via line 64 and nozzle 65 onto the bottom surface of core 51. Thereafter, when core 51 is joined with tissue layer 52 and subjected to microwaves from generator 62, the adhesive is activated or melted to bond tissue layer 52 to the interior surface of core 51. Alternately, tissue layer 52 may be bonded to core 51 by spraying the adhesive onto the interior surface of tissue layer 52 via line 66 and nozzle 67. Then, the core 51 and tissue layer 52 may be bonded together as they are subjected to the microwaves from generator 62.

Tissue layer 54 may also be bonded to the top surface of core 51 in a similar manner. As shown in FIG. 4, microwave activatable adhesive from a source 68 may be applied to the top surface of core 51 via line 69 and nozzle 70. Thereafter, tissue layer 54 is applied to core 51 and when subjected to the microwaves from generator 62, the adhesive will become activated and melt flowing into substrate 54 resulting in a strong bond between tissue layer 54 and core 51. Alternately, the same bonding result can be accomplished by spraying adhesive from source 68 via line 71 and nozzle 72 onto the interior surface of tissue layer 54. Once applied, the adhesive will absorb the energy from the microwaves created by generator 62 and bond tissue layer 54 to the top side of core 51. This laminate structure is then passed through the nip formed between two calendar rolls 86 and 87 which applies pressure against the laminate structure to ensure strong bonding between the substrates.

It is important to note that although FIG. 4 illustrates microwave generator 62 downstream of the laminating stations wherein tissue layer 52 is applied to the backside of core 51 and tissue layer 54 is applied to the topside of core 51 so that the adhesive is subjected to microwaves subsequent to applying the substrate to the core, generator 62 could just as easily be located so that the adhesive is subjected to the microwaves just prior to applying the substrates to the core, or simultaneously as applying the substrates to the core. The location of microwave generator 62 is thus a matter of choice depending upon the absorbent article being produced and the positioning of various components of the line for producing such an absorbent article. In fact, the application of the microwave activatable adhesive could actually occur at a location remote from the product line illustrated in FIG. 4. In other words, instead of spraying the adhesive onto the interior surfaces of tissue layers 52 and 54, these tissue layers 52 and 54 could be precoated with adhesive at a remote location, and thereafter activated on the manufacturing line, so that the spray assemblies illustrated in FIG. 4 would be optional on the system illustrated.

Finally, as illustrated, the nonwoven topsheet 56 and the impervious backsheet 58 may also be bonded utilizing microwave activatable adhesives. As illustrated, the topsheet 56 may be bonded to tissue layer 54 via adhesive fed from source 73 through line 74 and nozzle 75 onto the outer or top surface of tissue layer 54. Alternately, the adhesive from source 73 may be fed via line 76 and nozzle 77 onto the interior surface of nonwoven layer 56. Likewise, impervious backsheet 58 may be bonded to the underside of tissue layer 52 in a similar manner. Microwave activatable adhesive from source 78 may be fed via line 79 and nozzle 80 to be sprayed onto the lower surface of tissue layer 52. Alternately, the adhesive may be sprayed via line 81 and nozzle 82 onto the interior surface of backsheet 58.

Once joined into a laminate structure as illustrated in FIG. 3, the core 51, tissue layers 52 and 54, topsheet 56 and backsheet 58 are all subjected to microwaves generated from microwave generator 83 located downstream from this laminating station. The adhesive then absorbs the energy from the microwaves, becomes activated or melts to flow into the substrates., particularly topsheet 56 and backsheet 58, and bonds these substrates together. This laminate structure is then passed through the nip formed between two calendar rolls 84 and 85 which applies pressure against the laminate structure to ensure strong bonding between the substrates. Thereafter, the laminate structure is fed downstream for further processing into the desired finished article, i.e. a feminine care pad or diaper or the like.

A hot melt adhesive composition having ingredients in the following ranges provides a microwave activatable adhesive for use in the method of the present invention. More particularly, the adhesive composition useful in the method of the present invention has the following ingredients by weight;

about 10–90% of a polymer;
about 10–60% of a tackifying resin;
about 0–50% of a plasticizer;
about 0.1–2% of an antioxidant; the components totaling 100% by weight.

Any of a variety of available thermoplastic materials can be used as the polymer or in blends in the microwave activatable compositions in an amount from about 10% to about 90% by weight, preferably from about 15% to about 40%. Examples of such materials include ethylene based polymers, including ethylene/vinyl acetate, ethylene acrylate, ethylene methacrylate, ethylene methyl acrylate, ethylene methyl methacrylate, ethylene vinyl acetate carbon monoxide, and ethylene N-butyl acrylate carbon monoxide, polybutylene, high and low density polyethylene, polyethylene blends and chemically modified polyethylene, copolymers of ethylene and 1-6 mono- or di-unsaturated monomers, polyamides, polybutadiene rubber, polyesters such as polyethylene terephthalate, polybutylene terephthalate; thermoplastic polycarbonates, atactic polyalphaolefins, including atactic polypropylene, polyvinylmethylether and others; thermoplastic polyacrylamides, polyacrylonitrile, copolymers of acrylonitrile and other monomers such as butadiene styrene; polymethyl pentene, polyphenylene sulfide, aromatic polyurethanes; styrene-acrylonitrile, acrylonitrile-butadiene-styrene, styrene-butadiene rubbers, acrylontrile-butadiene-styrene elastomers, polyphenylene sulfide, A-B, A-B-A, A-(B-A)$_n$-B, (A-B)$_n$-Y block polymers wherein the A block comprises a polyvinyl aromatic block such as polystyrene, the B block comprises a rubbery midblock which can be hydrogenated, such as polybutadiene or polyisoprene, Y comprises a multivalent compound, and n is an integer of at least 3, and mixtures of said substances.

While the total styrene content of the polymers can be as much as 51 wt-% of the polymer, and since the polymers can have more than two A blocks for optimal performance, the total A block should be less than or equal to about 45 wt-% of the polymers, and, most preferably, is less than or equal to 35 wt-% of the polymer. In an S-B-S (styrene-butadiene-styrene) copolymer, the preferred molecular weight is about 50,000 to 120,000, and the preferred styrene content is about 20 to 45 wt-%. In an S-I-S (styrene-isoprene-styrene) copolymer, the preferred molecular weight is about 100,000 to 200,000 and the preferred styrene content is about 14–35 wt-%. Hydrogenating the butadiene midblocks produces rubbery midblocks that are typically converted to ethylene-butylene midblocks.

Such block copolymers are available from Shell Chemical Company, Enichem, Fina and Dexco. Multiblock or tapered block copolymers (the A-(B-A)$_n$-B type) are available from Firestone.

Preferred polymers for use as the microwave activatable adhesive are polyamides, polyesters, polyacrylates, carbon monoxide containing polymers, and combinations thereof.

These polymers quickly raise the temperature of adhesives containing them to provide usefulness on a feminine care pad or diaper manufacturing line.

The tackifying resins which are used in the adhesives of the present invention are those which extend the adhesive properties and improve the specific adhesion of the polymer. As used herein, the term "tackifying resin" includes:

(a) natural and modified rosin such as, for example, gum rosin, wood rosin, tall-oil rosin, distilled rosin, hydrogenated rosin, dimerized rosin and polymerized rosin;

(b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin;

(c) polyterpene resins having a softening point, as determined by ASTM method E28-58T, of from about 60° C. to 140° C., the latter polyterpene resins generally resulting from the polymerization of terpene hydrocarbons, such as the monoterpene known as pinene, in the presence of Friedel-Crafts catalysts at moderately low temperatures; also included are the hydrogenated polyterpene resins;

(d) copolymers and terpolymers of natural terpenes, e.g. styrene/terpene, α-methyl styrene/terpene and vinyl toluene/terpene;

(e) phenolic-modified terpene resins such as, for example, the resin product resulting from the condensation, in an acidic medium, of a terpene and a phenol;

(f) aliphatic petroleum hydrocarbon resins having Ring and Ball softening points of from about 60° to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Goodyear Tire and Rubber Company;

(g) aromatic petroleum hydrocarbons and the hydrogenated derivatives thereof;

(h) aliphatic/aromatic petroleum derived hydrocarbons and the hydrogenated derivatives thereof.

Mixtures of two or more of the above described tackifying resins may be required for some formulations. Although a range of 10–60% by weight tackifying resin may be used, the preferred range is 30% to 60%. An example of a commercially available tackifying resin which is useful for the present invention includes the resin which is identified commercially by the trade designation Nirez 2040. This resin is a terpene phenolic, and is available from Arizona Chemical Company.

A plasticizer can be present in the composition of the present invention in amounts of about 0% to about 50% by weight, preferably from about 10% to about 30%, in order to provide desired viscosity control without substantially decreasing the adhesive strength or the service temperature of the adhesive. A suitable plasticizer may be selected from the group which not only includes the usual plasticizing oils, such as mineral oil, but also olefin oligomers and low molecular weight polymers, glycol benzoates, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof. Other plasticizers may be used provided they have suitable compatibility and microwave absorption characteristics. The plasticizer that finds usefulness in the present invention can be any number of different plasticizers but Benzoflex 9-88, a dipropylene glycol dibenzoate manufactured by Velsicol, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications).

Waxes can be used in the composition of the present invention in amounts between 0–30%, and are used to reduce the melt viscosity of the hot melt construction adhesives without appreciably decreasing their adhesive bonding characteristics. These waxes also are used to reduce the open time of the composition without effecting the temperature performance. Among the useful waxes are:

(1) low molecular weight, that is, 1000–6000, polyethylene having a hardness value, as determined by ASTM method D-1321, of from about 0.1 to 120 and ASTM softening points of from about 150° to 250° F.:

(2) petroleum waxes such as paraffin wax having a melting point of from about 130° to 170° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) synthetic waxes made by polymerizing carbon monoxide and hydrogen such as Fischer-Tropsch wax; and (5) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred to use in the compositions of the present invention have a Ring and Ball softening point of 200° F. to 350° F. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent.

The present invention includes a stabilizer or antioxidant in an amount of from about 0.1% to about 2% by weight, but preferably from about 0.1% to 1%. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant is Irganox 1010, a tetrakis(methylene(3,5-di-teri-butyl-4-hydroxyhydrocinnamate))methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-ditert-butyl-4-hydroxyphenyl) propionate;

4,4'-methylenebis(4-methyl-6-tert butylphenol);

4,4'-thiobis(6-tert-butyl-o-cresol);

2,6-di-tert-butylphenol;

6- (4-hydroxyphenoxy)-2,4-bis(n-ocytlthio)-1,3,5-triazine;

2,4,6-tris(4-hydroxy-3,5-di-tert-butyl-phenoxy)-1,3,5-triazine; di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

Especially preferred as a stabilizer is pentaerythritol tetrakis-3(3,5-di-tert-butyl-4-hydroxyphenol) propionate.

The performance of these stabilizers may be further enhanced by utilizing, in conjunction therewith; (1) synergists such as, for example, as thiodipropionate esters and phosphites; and (2) chelating agents and metal deactivators as, for example, ethylenediaminetetraacetic acid, salts thereof, and disalicylalpropylenediimine.

The adhesive composition useful in the method of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

Optional additives may be incorporated into the adhesive composition in order to modify particular physical properties. These additives may include colorants, such as titanium dioxide and fillers such as talc and clay.

The invention is further illustrated by way of the examples which are set forth below.

EXAMPLE 1

The following tests were performed to determine broad categories of polymers that are microwave activatable, and to determine preferred activatable polymers for use in adhesives. Various individual plasticizers and resins were also tested.

Test method: Place 10 grams of adhesive in glass tube at ambient temperature (68° F.). Heat in commercial microwave unit for 1 minute at full power. Measure temperature of adhesive with a Pyrometer.

| TRADENAME | SUPPLIER | COMPOSITION | TEMP. @ 1 MIN. (° F.) |
|---|---|---|---|
| Vector 4411 | Shell | SIS polymer | 82° F. |
| Stereon 840A | Goodyear | SBS polymer | 82° F. |
| Elvax 240 | Dupont | Ethylene VinylAcetate polymer | 81° F. |
| Tone P767 | Union Carbide | Polycaprolactone polymer | 215° F. |
| NA820000 | Dupont | Ethylene n-butylacrylate polymer | 90° F. |
| Elvaloy HP 771 | Dupont | ENBA-carbon monoxide polymer | 262° F. |
| Elvaloy 741 | Dupont | EVA-carbon monoxide polymer | 280° F. |
| Hytrel 3078 | Dupont | Polyester-ether polymer | 220° F. |
| Amobond HM7000 | Amoco | Polyvinyl methyl ether polymer | 103° F. |
| Belland 2026 | Belland | Polyacrylate polymer | 135° F. |
| Primacore 5980i | Dow | Ethylene acrylic acid polymer | 85° F. |
| RX3716 | Dupont | Ethylene acrylic acid polymer | 89° F. |
| RX86-1 | Dupont | Ethylene methacrylic acid polymer | 90° F. |
| Polybutylene 8910 | Shell | Polybutylene polymer | 86° F. |
| Dynapol 1227 | Huls | Polyester polymer | 110° F. |
| Macromelt 6245 | Henkel | Polyamide polymer | 97° F. |
| Be²-185 | Bareco | Microcrystalline wax | 82° F. |
| Epolene C16 | Eastman | Acid modified wax | 84° F. |
| Atmer 129 | ICI | Glycerol Monostearate | 120° F. |
| SMO | RhonePoulenc | Sorbitan Monooleate | 225° F. |
| SAIB | Eastman | Sucrose acetate isobutyrate | 140° F. |
| Kaydol | Witco | Mineral oil | 87° F. |
| Monoplex S75 | C. P. Hall | Epoxidized ester oil | 266° F. |
| Plasthall TOTM | C. P. Hall | Trimellitate oil | 130° F. |
| Tagmer 809 | C. P. Hall | PEG diester oil | 260° F. |
| Paraplex G40 | C. P. Hall | Polymeric polyester oil | 220° F. |
| Plasthall 7050 | C. P. Hall | Dialkylether diester oil | 320° F. |
| Plasthall 200 | C. P. Hall | Diakylether aromatic ester oil | 320° F. |

-continued

| TRADENAME | SUPPLIER | COMPOSITION | TEMP. @ 1 MIN. (° F.) |
|---|---|---|---|
| Benzoflex 9-88 | Velsicol | Benzoate ester oil | 340° F. |
| Plasthall BSA | C. P. Hall | Aromatic sulfamide oil | 330° F. |
| Nirez V2040 | Arizona | Terpene phenolic resin | 82° F. |
| Unitac R100L | Union Camp | Rosin ester resin | 82° F. |
| Zonatac 85L | Arizona | Styrenated terpene resin | 81° F. |
| Endex 155 | Hercules | Styrene resin | 83° F. |

Adhesive Blends:

| DESIGNATION | COMPOSITION | TEMP. @ 1 MIN. (° F.) |
|---|---|---|
| A | 55% Nirez V2040/24% Tone P767/20% Benzoflex 9-88/1% Irganox 1010 | 183° F. |
| B | 40% Unitac R100L/39% Elvaloy HP771/9% Be$^2$-185/10% Benzoflex 9-88/1% Atmer 129/1% Irganox 1010 | 236° F. |

From the above tests it was determined that no resins tested had any significant activation. On the other hand, many different polymers and plasticizers, specifically oils, are activatable. It appears that the preferred polymers are polyamides, polyesters, polyacrylates and combinations thereof.

EXAMPLE 2

Construction Application:

Adhesive was applied to treated polyethylene (diaper backsheet). The adhesive was slot coated to the polyethylene with an adhesive thickness of 1.0 mil. The adhesive temperature was 275° F. Later, a nonwoven (diaper topsheet) was placed on top of the coated polyethylene. This laminate was placed into a commercial microwave and heated for 1 minute. Instron peels were run with a cross-head speed of 12 inches/minute. The nonwoven was peeled from the polyethylene and the bond strength measured on samples both with and without microwave energy exposure.

The peel strengths are as follows:

| ADHESIVE | MICRO-WAVE EX-POSURE? | AVERAGE PEEL STRENGTH (gm) | STANDARD DEVIATION | FAILURE MECHANISM |
|---|---|---|---|---|
| H4073 (Standard construction) | No | 101.6 | 21.1 | Adhesive from NW |
| H4073 (Standard construction) | Yes | 134 | 32.9 | Adhesive from NW |
| Blend A (Microwave sensitive) | No | 115.3 | 11.1 | Adhesive from NW |
| Blend A (Microwave sensitive) | Yes | 403 | 17.9 | Cohesive |

Adhesive failure from the nonwoven suggests that the adhesive is not bonding to the secondary substrate to which it was later put in contact. Cohesive failure suggests that the adhesive has good adhesion to both substrates, and the bond failure is due to internal strength of the adhesive. After exposure to microwave energy, the standard adhesive does not improve in adhesion to the nonwoven. The adhesive formulated to be sensitive to microwave energy melts and forms a good bond to both substrates.

This example also demonstrates that a microwave sensitive adhesive could be coated onto substrates prior to use and later "activated" on the diaper line.

EXAMPLE 3

Core application:

Powdered material was spread onto a section of a diaper core. A tissue layer was placed on top of the core and powder. The composite was placed into a commercial microwave and heated for one minute. After heating, the tissue was peeled in an Instron from the core material.

EXAMPLE 3

| ADHESIVE | MICRO-WAVE EX-POSURE? | AVERAGE PEEL STRENGTH (gm) | STANDARD DEVIATION | FAILURE MECHANISM |
|---|---|---|---|---|
| Elvaloy 741 | No | 6.3 | 4.1 | No bond to tissue |
| Elvaloy 741 | Yes | 42.1 | 11.2 | No bond failure, core separation |
| Polywax 2000 | No | 7.2 | 3.8 | No bond to tissue |
| Polywax 2000 | Yes | 6.1 | 5.3 | No bond to tissue |

A failure mechanism of "no bond to tissue" suggests that the powdered material did not have any adhesion to substrates. In fact, it would simply fall off when the sample was placed on an angle. With the Elvaloy 741 after exposure to microwave energy, the powder melted and flowed both into the core and into the tissue fibers. When running the peel strength test, the bond was not broken between the tissue and core. A section of the core was simply peeled away from the rest of the core material.

This example demonstrates that a microwave sensitive material in dry form could be either mixed with the absorbent fluff in the hammermill or placed on top or bottom of the core material and then "activated" on the line.

We claim:

1. A method of bonding an absorbent core to another substrate of a disposable nonwoven absorbent article including the steps of:

mixing an absorbent material with a microwave activatable adhesive, said adhesive includes as components thereof about 10–90% by weight of a polymer, about 10–60% by weight of a tackifying resin, about 0–50% by weight of a plasticizer, and about 0.1–2% by weight of an antioxidant, the components totaling 100% by weight;

forming the absorbent material and adhesive into an absorbent core;

applying a substrate to at least one surface of said absorbent core; and subjecting said adhesive to microwaves to activate the adhesive and bond said substrate to said absorbent core.

2. The method of claim 1 wherein the step of subjecting the adhesive to microwaves occurs prior to applying the substrate to said at least one surface of said absorbent core.

3. The method of claim 1 wherein the step of subjecting the adhesive to microwaves occurs subsequent to applying the substrate to said at least one surface of said absorbent core.

4. The method of claim 1 wherein the step of subjecting the adhesive to microwaves occurs simultaneously with applying the substrate to said at least one surface of said absorbent core.

5. The method of claim 1 wherein said substrate is selected from the group consisting of nonwoven fabric, tissue, absorbent fluff, superabsorbents, elastics, a polyolefin, and combinations thereof.

6. The method of claim 5 wherein said polyolefin comprises a polyethylene or polypropylene layer.

7. The method of claim 1 wherein said adhesive includes as one component thereof a polymer selected from the group consisting of a polyamide, a polyester, a polyacrylate, a carbon monoxide containing polymer, and combinations thereof.

8. The method of claim 1 wherein said absorbent material is selected from the group consisting of absorbent cellulosic material, polyolefins, superabsorbent polymers, polyesters, and combinations thereof.

9. The method of claim 1 wherein said adhesive is in the form of powder, flakes, grains, or fibers.

10. The method of claim 1 wherein said adhesive is a hot melt adhesive.

11. A method of bonding a first substrate to a second substrate of a disposable nonwoven absorbent article, including the steps of:
feeding a first substrate and a second substrate, said second substrate to be bonded to said first substrate, toward a laminating station;
applying a microwave activatable adhesive to a surface of at least one of said first and second substrates prior to said substrates reaching said laminating station, said adhesive includes as components thereof about 10–90% by weight of a polymer, about 10–60% by weight of a tackifying resin, about 0–50% by weight of a plasticizer, and about 0.1–2% by weight of an antioxidant, the components totaling 100% by weight;
combining said first and second substrates and said adhesive together at said laminating station to form a laminate; and
subjecting said adhesive to microwaves to activate the adhesive and bond said second substrate to said first substrate.

12. The method of claim 11 wherein the step of subjecting the adhesive to microwaves occurs prior to forming said laminate.

13. The method of claim 11 wherein the step of subjecting the adhesive to microwaves occurs subsequent to forming said laminate.

14. The method of claim 11 wherein the step of subjecting the adhesive to microwaves occurs simultaneously with forming said laminate.

15. The method of claim 11 wherein said first and second substrates are each independently selected from the group consisting of nonwoven fabric, tissue, absorbent fluff, superabsorbents, elastics, a polyolefin and combinations thereof.

16. The method of claim 15 wherein said polyolefin comprises a polyethylene or polypropylene layer.

17. The method of claim 11 wherein said adhesive includes as one component thereof a polymer selected from the group consisting of a polyamide, a polyester, a polyacrylate, a carbon monoxide containing polymer and combinations thereof.

18. The method of claim 11 wherein said adhesive is dry when applied to said surface.

19. The method of claim 11 wherein said adhesive is in the form of powder, flakes, grains, or fibers.

20. The method of claim 11 wherein said adhesive is a hot melt adhesive.

21. A method of bonding absorbent material together for use as an absorbent core of a disposable nonwoven absorbent article including the steps of:
mixing an absorbent material with a microwave activatable adhesive, said adhesive includes as components thereof about 10–90% by weight of a polymer, about 10–60% by weight of a tackifying resin, about 0–50% by weight of a plasticizer, and about 0.1–2% by weight of an antioxidant, the components totaling 100% by weight;
forming the absorbent material and adhesive into a non-self-supporting absorbent core; and
subjecting said core and adhesive to microwaves to activate the adhesive and bond said absorbent material together to form a cohesive self-supporting absorbent core.

22. The method of claim 21 further including the step of applying a substrate to at least one surface of the cohesive self-supporting absorbent core.

23. The method of claim 22 wherein the step of subjecting the core and adhesive to microwaves occurs prior to applying the substrate to said at least one surface of said self-supporting absorbent core.

24. The method of claim 22 wherein the step of subjecting the core and adhesive to microwaves occurs subsequent to applying the substrate to said at least one surface of said self-supporting absorbent core.

25. The method of claim 22 wherein the step of subjecting the core and adhesive to microwaves occurs simultaneously with applying the substrate to said at least one surface of said self-supporting absorbent core.

26. The method of claim 22 wherein said substrate is selected from the group consisting of nonwoven fabric, tissue, absorbent fluff, a polyolefin, superabsorbents, elastics, and combinations thereof.

27. The method of claim 26 wherein said polyolefin comprises a polyethylene or polypropylene layer.

28. The method of claim 21 wherein said adhesive includes as one component thereof a polymer selected from the group consisting of a polyamide, a polyester, a polyacrylate, a carbon monoxide containing polymer, and combinations thereof.

29. The method of claim 21 wherein said absorbent material is selected from the group consisting of absorbent cellulosic materials, polyolefins, superabsorbent polymers, polyesters, and combinations thereof.

30. The method of claim 21 wherein said adhesive is in the form of powder, flakes, grains, or fibers.

31. The method of claim 21 wherein said adhesive is a hot melt adhesive.

* * * * *